United States Patent
Linford et al.

(10) Patent No.: US 9,939,351 B1
(45) Date of Patent: Apr. 10, 2018

(54) SOLID PHASE COATINGS FOR MICROEXTRACTION

(71) Applicant: Moxtek, Inc., Orem, UT (US)

(72) Inventors: Matthew R. Linford, Orem, UT (US); Anubhav Diwan, Provo, UT (US); Bhupinder Singh, Provo, UT (US)

(73) Assignee: Moxtek, Inc., Orem, UT (US)

( * ) Notice: Subject to any disclaimer, the term of this patent is extended or adjusted under 35 U.S.C. 154(b) by 617 days.

(21) Appl. No.: 14/563,981

(22) Filed: Dec. 8, 2014

Related U.S. Application Data

(60) Provisional application No. 61/963,562, filed on Dec. 6, 2013, provisional application No. 62/077,479, filed on Nov. 10, 2014.

(51) Int. Cl.
| | | |
|---|---|---|
| *G01N 1/22* | (2006.01) |
| *G01N 1/10* | (2006.01) |
| *G01N 33/00* | (2006.01) |
| *C23C 14/34* | (2006.01) |
| *C23C 14/10* | (2006.01) |

(52) U.S. Cl.
CPC ........... *G01N 1/2214* (2013.01); *C23C 14/10* (2013.01); *C23C 14/34* (2013.01); *G01N 1/10* (2013.01); *G01N 33/0011* (2013.01)

(58) Field of Classification Search
CPC ..... G01N 1/4055; G01N 2030/524–2030/525; G01N 2030/567; G01N 2030/009; G01N 30/96
See application file for complete search history.

(56) References Cited

PUBLICATIONS

Wang et al., ZnO nanorod array solid phase micro-extraction fiber coating: fabrication and extraction capability, Oct. 2009, IOP Publishing, Nanotechnology 20 465702.*

* cited by examiner

*Primary Examiner* — Erika J Villaluna
(74) *Attorney, Agent, or Firm* — Thorpe, North & Western, LLP

(57) ABSTRACT

An extractive system, such as SPME, has an adsorptive phase in the form of a porous coating that has essentially vertical, mutually supporting, columnar structures with nanospaces at the boundaries of the grains.

20 Claims, 12 Drawing Sheets

Before　　　　　　　　After

SOLID PHASE COATINGS FOR MICROEXTRACTION

CROSS REFERENCE TO RELATED APPLICATIONS

Priority is claimed from U.S. Provisional Patent Application 61/963,562, filed Dec. 6, 2013, which hereby incorporated by reference.

Priority is claimed from U.S. Provisional Patent Application 62/077,479, filed Nov. 10, 2014, which hereby incorporated by reference.

BACKGROUND

Solid phase microextraction (SPME), first introduced by Arthur and Pawliszyn in 1990, is a solvent-free, cheap, fast and easy technique that integrates sampling, isolation and concentration of analytes in one single step. It is widely used to extract an array of volatile and semi-volatile organic compounds.

SPME is a sample preparation technique that extracts different kinds of analytes (including both volatile and non-volatile) from different kinds of liquid or gaseous media. In general, the quantity of analyte extracted by the coating is proportional to its concentration in the sample matrix.

SPME is used widely to detect components in a sample in very small and trace amounts. These include, for example, in food analysis, such as for residual contaminants (pesticides/ herbicides), quality control, characterization and forensic analysis, in in-vivo analysis, such as diagnostic tests, pharmacokinetic studies, and drug bioavailability in environment samples, such as water or air for contaminants and pollutants, and in biologicals, such as body fluid analysis, and breath analysis.

In an SPME assembly, the coated fiber is inside a septum piercing needle. The septum of a vessel containing the sample is pieced and the coated fiber is extended to expose same to a liquid sample or to air above the sample (headspace). The coating is designed to retain target compounds.

The fiber is then retracted into the microtube. The septum associated with the injection port of a separation/analysis instrument, such as a gas-chromatography system (SPME-GC), is then pierced, the fiber reexposed, and the target compounds are desorbed into a gas stream to form a tight sample plug at the entrance of a relatively cold column. The fiber is then retracted and removed. Using temperature programming, the column temperature is ramped up, hence separating the analytes.

SPME can also be hyphenated to HPLC (High-performance liquid chromatography), CE (Capillary electrophoresis), and other analytical techniques. In case of SPME-LC, for example, the desorption of analytes is achieved via changing the polarity of the mobile phase.

A key component of the fiber, which is often made of silica or metal, is the coating. The coating in current commercial systems is often an absorbent. With absorbent coatings analyte molecules are taken up by the volume and become incorporated into a bulk phase. The coating may be a liquid phase with the absorbed analyte molecules in solution. Commonly used coatings include polydimethylsiloxane (PDMS), polyethylene glycol (PEG, carbowax) and polyacrylate.

Major problems with these coatings involve solvent incompatibilities that may lead to swelling in organic phases. The life of the fiber is often short, due to the fragile nature of the fiber substrate, especially if it is silica. Other problems include high cost, a limited number of compounds that can be extracted into the coating, and the relatively low thermal, and mechanical stability of the coatings. In addition, the coatings may not have strong adhesion to the substrate. This problem has been somewhat mitigated by applying adhesion or bonding layers between the substrate and extraction phase of the coating. However, these problems persist.

Another problem with absorptive coatings is carryover, where analyte is retained from previous uses of the fiber that may show up in subsequent analyses, and, therefore, compromise the results of the subsequent analyses. The desorb conditions are usually designed to desorb analyte as close to 100% as practically possible, but with some coatings significant analyte amounts are retained and carried over into the next sampling.

Adsorbent coatings, in contrast to absorbent coatings, involve retention of analyte molecules to a solid surface (not to the volume) of a solid. Effective adsorbents have a high surface area, which can be provided by solids with high porosity with small pores. Adsorbent coatings have been used in several applications. Solid adsorbent coatings include carbowax-divinylbenzene, PDMS-divinylbenzene, and carboxen-PDMS.

As solid coatings involve adsorption of analytes on a surface, the process is usually faster as compared to liquid coatings. On the flip-side, lower porosity and competitive adsorption may limit the extraction efficiencies of solid phases. Various techniques are now being used to make these solid phases, including sol-gel chemistry, electrodeposition, and attaching nanoparticles to the fiber using thermo-stable adhesives. All of these coatings suffer from various drawbacks, including very long preparation times, limited mechanical, thermal, and solvent stability, the ability to extract limited numbers of compounds, and short lifetimes of the fibers.

In commercial coatings such as CAR-PDMS, PDMS-DVB, particles with adsorptive surfaces have been embedded into absorptive coatings. While these may have modified sorptive properties, they suffer from similar problems as absorption coatings.

In general, there are various methods for applying coatings upon substrates, each with varying properties. One class of coating systems involves physical vapor deposition. This process involves depositing atoms or molecules in the vapor phase on a substrate. Examples include sputter deposition, electron beam evaporation, thermal evaporation, and pulsed laser deposition.

All physical vapor deposition systems require production of a precursor vapor material that then condenses upon and is retained on a substrate to form a coating. The vapor can be created by, for example, thermal evaporation, electron-beam, evaporation, sputtering, including DC sputtering and, RF sputtering, cathodic arc vaporization, laser ablation, decomposition of a chemical vapor precursor. All of these are contemplated by the present method.

At a relatively higher gas pressure, the ejected atoms from the target can impact with other atoms or molecules on its path and travel to the substrate diffusively, impacting the substrate from random directions. It has already been shown that if atoms impact the substrate obliquely, due to, for example, substrate orientation to the target or to higher pressure, "defects" in the dense coating can occur. At these conditions it has been observed that films with columnar grains of different densities will form.

A method known as glancing angle deposition (GLAD), involves exploitation of the shadowing effect to create deposited films with various properties. The flux of vapor relative to the substrate is oblique, which results in the growth of slanted columnar microstructures. By manipulating the direction of flux during deposition, various columnar shapes have been obtained, with a wide range of porosity.

SUMMARY

A problem with finding a suitable SPME coating that is firmly bonded to the substrate, is chemically stable to the environment that it encounters, shows little or no carryover between runs, shows appropriate chemical affinity for analytes of interest, and has sufficient thermal stability for multiple cycles of adsorption and desorption by heating while having and maintaining good adsorption properties. The amount of analyte adsorbed by the coating is proportional to the concentration in the sample. Accordingly, sensitivity of the SPME analysis is proportionally increased by increasing the surface area of the SPME coating, which should increase the amount of analyte retained on the surface.

An aspect is a method for manufacturing an extractive apparatus in which analytes are adsorbed onto an extractive phase and subsequently desorbed. Nevertheless, and without being limited by theory, the stationary phases deposited onto these porous, adsorbant coatings, e.g., a silane, may possess a measure of absorptive properties. The method for manufacturing comprises, providing a substrate with a surface, coating the substrate surface with an adsorptive porous phase to create the extractive phase on the surface. The coating is applied by producing a vapor of a coating precursor material by a sputtering method, and allowing the vapor to deposit upon the substrate surface under suitable temperature conditions. These condition are where the deposition temperature is defined as $T/T_m < 0.3$, where T is the film deposition temperature, $T_m$ is the film melting point temperature, where T and $T_m$ are measured in absolute temperature (degree Kelvin). Under these conditions there is little mobility of the atoms, and atoms in the vapor impinge upon the substrate surface at an oblique angle to form a porous coating with columnar nanostructure, with nanospaces at the boundaries between adjacent columns to form porosity.

The conditions of applying the coating have to be carefully controlled. Attempts were made to make a coating on a SPME needle using an oblique angle deposition method. Using an electron beam vapor generation, deposition was made upon a slanted substrate. The resulting coatings showed porosity and initially performed well. But, with each subsequent use, the performance was significantly degraded. Microscopic examination of the surfaces revealed the coating with each use was significantly removed, presumably by abrasion. Basically, the deposited coating is not robust and is too fragile for SPME extraction, or similar processes.

It has been found, however, that robust porous coatings can be made. These coatings are characterized by a columnar structure, but the coatings differ from typical GLAD/oblique deposition microstructures in the following ways;
(1) The columnar structures are essentially vertical relative to the substrate surface, rather than oblique or slanting,
(2) The boundaries between the columnar structures are spaced, but columns are also close enough that adjacent columns are mutually supporting. This and the vertical alignment is believed to contribute to the robustness of the coatings. While adjacent columnar structures may or may not be interlocking, there is sufficient physical or mechanical interaction between the columnar structures that a columnar structure is at least in part supported and maintained on the substrate by its neighboring columnar structures.
(3) The deposited coatings are tapered with the thickness of the columnar structured film decreasing as it deposits further from the sputtering target, or the vapor source. In SPME needles, the fiber substrate is pointed in the general direction of the target. The thickness of the coating is circumferentially constant, but tapers down the further from the point of the needle. The point of the needle is pointed generally at the sputter target, with the coating depositing more thick at the point. By "pointed generally at the sputter target" is meant that the orientation of the needle during deposition is sufficient to form the tapered coating as described. Orientations that are not so generally pointed lead to uneven coatings that vary from constant circumferential thickness to the point that the function of the coating is material compromised.
(4) The deposited coatings are applied using a sputter physical vapor deposition method. Sputter deposition at carefully chosen conditions results in the vertical, mutually supporting, columnar structures in the porous coating, which, to the knowledge of the applicants, has not been achieved by other methods. Sputtering, as compared to other vapor deposition methods, may also contribute in unknown and different ways to the robustness and porosity of the coating.

By 'essentially vertical' is meant the columnar structures are close to perpendicular to the surface plane of the substrate. When columnar structures are not essentially vertical the interaction and mutual support of the neighboring columnar structures declines to where any columnar structure is essentially supported only at its attachment to a substrate. It is believed that these slanting, oblique structures lack sufficient support upon the substrate for a robust coating required for an extractive phase, such as SPME.

Another aspect is a method for extracting analytes from a gas or liquid phase comprising exposing the phase to an extractive adsorptive phase comprising a porous coating upon a substrate. The coating has essentially vertical, mutually supporting columnar nanostructures with nanospaces between adjacent columnar structures.

Another aspect is an apparatus in which analytes are adsorbed onto an extractive phase and subsequently desorbed. The apparatus comprises an extractive adsorptive phase comprising a porous coating upon a substrate. The coating has essentially vertical, mutually supporting columnar nanostructures with nanospaces between adjacent columnar structures. The apparatus also includes structure for introducing liquid or gas containing analytes to the surface for sufficient time to allow the analytes to adsorb upon the extractive phase, structure for desorbing analytes from the surface into a gas stream, and a detector for detecting analytes in the gas stream.

The characteristics of coatings of the present method as used in extraction, such as SPME, are;
  Highly porous with high extraction efficiency,
  Relatively thinner than conventional SPME coatings, which should show faster extraction and desorption.
  Robust and adherent with an increased life.
  Controlled thickness that is reproducible, and strongly adherent to the substrate.
  Chemically inert and unaffected by organic solvents.
  Usable for SPME-LC, SPME-CE, SPME-MALDI and other hyphenated analytical techniques.
  Relatively higher mechanic and thermal stability with a longer life, Applicability to extraction of an array of compounds.

As of the date of this application (December 2014) the only method known to the applicant that can form the essentially vertical, tapered, mutually supporting, columnar structures of the present coatings is sputter deposition. At this time, based upon preliminary studies and attempts, coatings usually deposited by GLAD-type process, are believed to be too fragile. It may be possible to adapt other physical vapor deposition methods, noted above, to form the essentially vertical, tapered, mutually supporting, columnar structures, found in the present coatings, but it cannot be predicted whether any processes and adaptations will be successful, and what such process and adaptions to form a successful coating will be.

In sputter deposition material is sputtered or ejected from a target to create a vapor of a coating precursor material. The material is deposited as a coating, that may be of the same or similar composition as the target, or be a different composition, or a mixture of same and altered materials. The deposited particles that deposit may also react with each other or other particles. For example, depositing silicon may result in some silicon oxide in the coating. Sputtering may take place simultaneously from more than one target of same or different materials, and reactive sputtering (sputtering in the presence of a reactive gas) is possible. The vapor is formed by bombarding the target with a plasma, such as of Argon ions. In many sputtering applications, the ideal is to have the ejected particles fly in generally straight lines without collision or interaction with other particles before they impact upon the substrate. The result is a thin dense coating on the substrate with negligible porosity, which is usually the desired result for electronic and optical applications. This requires a low gas pressure.

The SPME coating described herein is deposited using a sputtering physical vapor deposition method. Sputtering is one of physical vapor processes used to deposit layers of material atom-by-atom or molecule-by-molecule on a solid surface. In general, these processes operate at pressures well below atmospheric pressure. The deposited layers can range from a thickness of one atom up to millimeters, forming freestanding structures. Multiple layers of different materials can be deposited. These processes are good for depositing thin, dense and even coatings, and are used extensively in the semiconductor industry to deposit thin films of various materials for integrated circuit processing. Extensive use is also found for optical coatings, coatings on plastic (CDs), tool bit coatings, and the like.

The present coatings are achieved by carefully controlled conditions relating to diffusional relaxation and the angular distribution of the incident particle flux upon the substrate. Suitable conditions are where a significant fraction of the incident atoms impact the surface obliquely. With sufficient atoms incident at these angles there is a shadowing effect originating from obliquely incident atoms being preferentially deposited at hills on the surface, resulting in the porous coating growing in the form of columnar grains.

A key aspect of these depositions is that they take place at temperatures in which there is little mobility of the atoms that impinge upon the surface. Various structure zone models have been proposed to describe the effects of temperature on microstructure in sputtered coatings. See, for example: 'The microstructure of, sputter-deposited coatings' by John A. Thornton in J. Vac. Sci. Technol. A 4(6) 1986, pgs. 3059-3065. At relatively low temperatures, T, compared to the film melting point, $T_m$, i.e., at $T/T_m<0.3$, where these temperatures are in Kelvin, structures consisting of columns separated by voids are typically observed.

An important aspect of these coatings is that they have a high surface area, i.e., the surface area of the sputtered coatings is high, like a porous structure. While not being bound to any theory, it is believed that the high surface area derives in part from nanospaces that occur between the grains Another important aspect is a unique process by which the porous coating on the SPME is deposited. The fiber is pointed in the general direction of the sputter target (the source of the deposited atoms). Without being limited by theory, it is believed that this creates a shadowing effect leading to columnar grains that uniformly coat the circumference of the fiber, where the thickness of the SPME extractive coating is thicker at the end of the fiber that is nearest the sputter target.

Another aspect of the invention is that after the coating is deposited on the fiber, the fibers can be further processed or modified. For example, for a silicon or silica fiber the fiber surface can be silanized. Hydroxylation of a sputtered silicon or silica surface introduces additional silanol groups to its surface that are used to attach a $C_{18}$ silane, which eventually renders the surface hydrophobic. The presence of silanol groups allows one to use silanization chemistry to introduce various functional groups to surfaces and hence to be able to extract an array of compounds. Another example is reacting a SPME fiber with a deposited coated of zirconia with a phosphonate.

Another aspect is a method for nanoporous SPME coatings via physical vapor deposition (sputtering). In an exemplary embodiment, silicon is deposited on fiber substrates hanging in a vertical direction so that they are approximately perpendicular to the target. The gas pressure in the chamber is adjusted so that the fiber-target distance is at least one mean free path. In general, conditions are created to produce the shadowing effect that causes a porous coating to deposit with the previously described columnar structures. The orientation of the substrate and the gas pressure are significant ways to create this shadowing effect. However, it is contemplated that other adjustments to the sputtering environment may create or contribute to the shadowing effect.

In the examples, the target material is silicon, and hence the material of the coating, includes silicon. However, it is contemplated that various other materials can be deposited by physical vapor deposition with similar results, making suitable adherent, coatings with similar columnar high-surface structures . . . . Suitable materials include, for example, silica, silicone, carbon, aluminum, alumina, titanium, titania, lead, lead oxide, tin, tin oxide, iron, iron oxide, zirconium, zirconia, magnesium, bismuth, tellurium, selenium, chromium, or sputtering targets with combination of different metals like silicon carbide, silicon, nitride, bismuth tellurium selenium and others.

In the specification and in the claims, the term "vapor atoms" includes atoms in vapor phase. "Vapor atoms" and may also include molecules inorganic or organic of the same or different elements. The "vapor atoms" in a deposition may all be the same or they may be different. Any material that can be made into or can generate a vapor or particles in vapor phase are "vapor atoms" and are contemplated in the present process.

Materials with interesting or unique extraction capabilities that can be sputtered, co-sputtered, or reactively sputtered could potentially be deposited onto an SPME fiber. Even polymeric materials can be sputtered and could have useful selectivities. Selection of the coating material can yield properties adapted for a particular application. For example, carbon and zirconia coatings could find potential as a product in SPME-LC, as these coatings would be stable under extremes of pH and temperature and would be solvent compatible. It is also contemplated that at least a portion of the coated materials, may react or otherwise be different from the target material. For example, when silicon is sputtered, the coating surface may be oxidized. It is also contemplated that different materials may be sputtered sequentially to create an SPME coating.

The coating in the in the example was on silica substrates (fibers). It is contemplated that there are other substrates, that can be sputtered coated and have the suitable chemical and physical properties. For example, flexible stainless steel fibers (Stableflex™) could be used. Aluminum, copper, tin, chromium, nickel and other robust metal substrates could be used to support an extractive phase layer.

The present fibers can be used in SPME-GC, SPME-CE, SPME-MALDI, SPME-LC and other hyphenated analytical techniques.

The present fibers could find application in solid phase dynamic extraction and needle trap extraction. The inside diameter of the needle could prevent enough vapor flux from reaching the surface to warrant adequate coating. One of the possible variables could be to coat a small diameter fiber and fix it inside the tube/needle to carry out in-tube SPME or even needle trap (the coated fiber can have a snug fit with the needle)

The present approach can be used to make highly porous coatings for fabricating sensing devices.

The present approach can be used for making substrates for matrix-assisted laser desorption/ionization (MALDI) or similar desorption mass spectrometry techniques. The back (rough) side of a silicon wafer can be silanized with a fluorosilane. The back side of the wafer is used for the roughness—added hydrophobicity. The surface is then masked so that one have ca. 1 mm patches remaining. One could sputter silicon onto these areas to give a porous coating.

Sputtered UTLC plates can be fabricated using the same approach for thin layer chromatography. Co-sputtering of silicon and carbon can be carried out, followed by oxidation of carbon to yield silica based porous UTLC plates.

The present approach can be used to sputter metals/metal oxides in channels of microfluidic/nanofluidic devices, such as point of care devices. This extraction phase could be modified using different reactions (silanization chemistry in case of silica coatings; phosphonate reactions on aluminum phases to extract basic compounds etc.) to get desired selectivities. One would expect these sputtered coatings to be useful in sensing, enrichment and/or separation step in a microfluidic device. The highly porous surfaces with vertical columnar structures, that are stable with adequate loading capacity for use in microfluidic devices.

SMPE-GC is an important application for the present fibers. However, the present method is applicable for other applications, such as to coat stir bars, vessel walls, stirrers, disks, and membranes used in SPME or related extraction methods.

The surface of a sputtered silicon coating can be modified to render unique selectivities using silane chemistry, via solution or vapor deposition. n-octadecyldimethylmethoxysilane, n-octadecyldimethylchlorosilane, phenyldimethylmethoxysilane, a PFP (pentafluoro phenyl) silane, a biphenyl silane, a cyano silane, an amino silane, n-octyldimethylmethoxysilane, n-octyldimethylchlorosilane, diphenyldimethoxysilane are some of the many silanes that can render interesting properties to the coatings. Silanes contemplated include monofunctional silanes and multifunctional silanes (such bi-, and tri-functional). Exemplary silanes include, APTES ((3-aminopropyl)triethoxysilane), n-octadecyltrichlorosilane, n-octadecyltrimethoxysilane, and n-octadecylmethyldiethoxysilane.

The binding of alkyl or perflourinated phosphonates have been shown in the literature to bind to different metals or metal oxides like alumina, stainless steel zirconia, or others. In the present process, the sputtered coated fibers can be given different funtionalities by dipping in a solution of long chain alkyl or perflourinated phosphonates or silanes to prepare robust SPME fibers.

In addition to mono-functional $C_{18}$silane, other silanes are contemplated, such a multifunctional, for example, bi- or tri-functional silanes.

Figure 5:
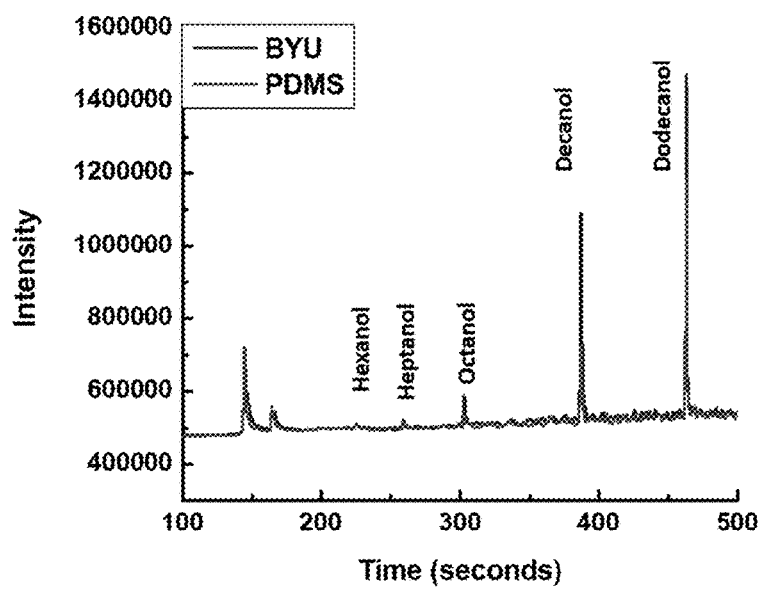

As with the alkanes, the separation of alcohols was performed at University of Tasmania where we got the same results (FIG. 5). Sputtered fibers were performing better than the commercial PDMS fibers, especially in the high mass regime. The fact that the present fibers were working in different labs and giving superior results than the commercial counterparts is encouraging and vouches for the robustness and usefulness of the product.

FIG. 5. Primary alcohols (hexanol, heptanol, octanol, decanol and dodecanol) extracted using present sputtered ca. 1 μm three hour sputtered fiber and PDMS 7 μm fiber. Present sputtered fiber shows that it gives more response for the test mix used.

Figure 6:
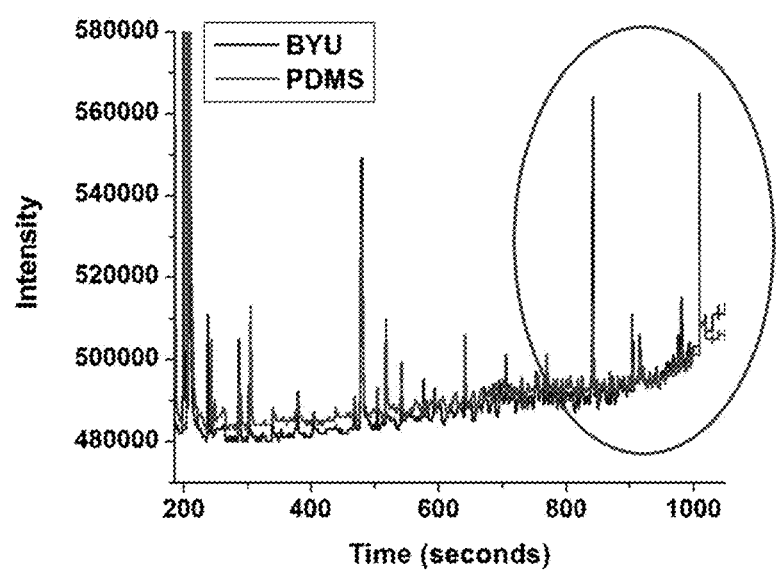

FIG. 6. Head space extraction of components of a commercial beer sample using present sputtered and PDMS 7 μm fibers.

Figure 7:
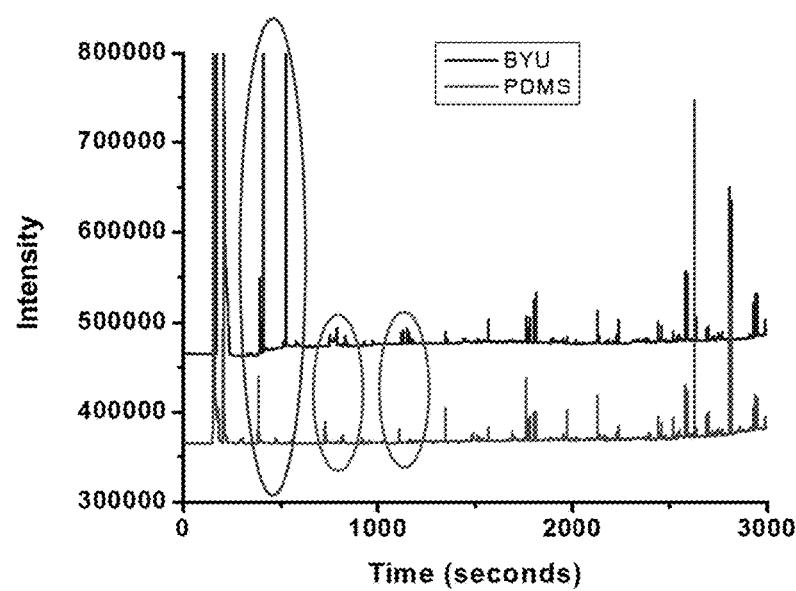

FIG. 7. Head space extraction of components of a sea water extract using present sputtered ca. 1 μm and PDMS 7 μm fibers.

Figure 8:
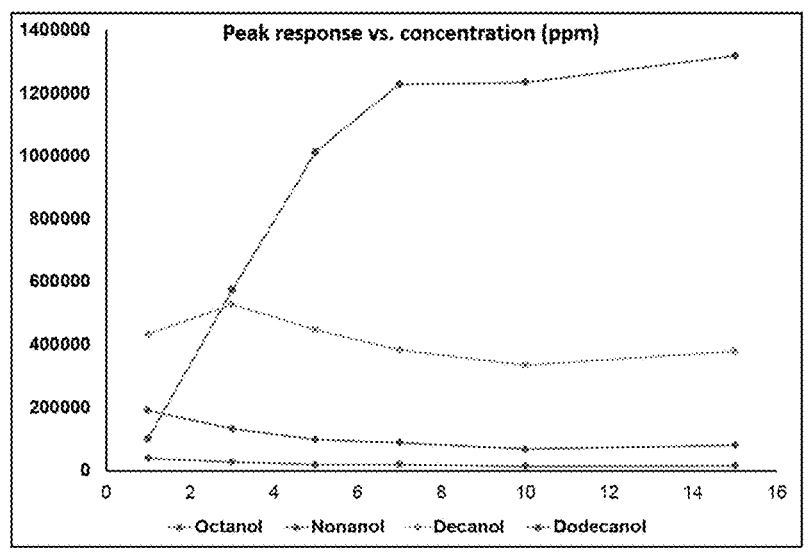

FIG. 8. Extraction profile of present sputtered 1 μm fiber using $C_8$, $C_9$, $C_{10}$ and $C_{12}$ primary alcohol using different extraction times: 1, 3, 5, 7, 10, and 15 minutes.

Figure 9:
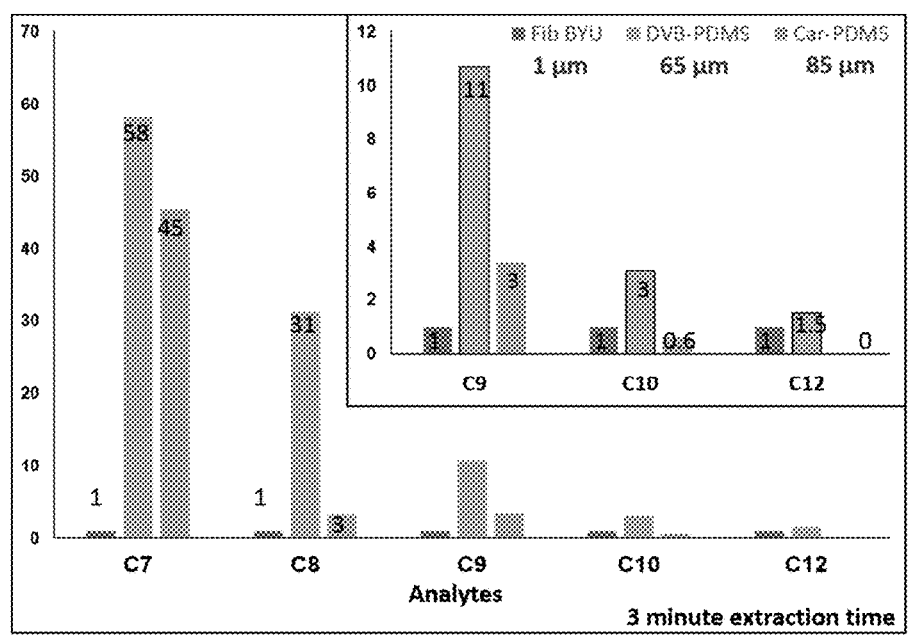

FIG. 9. Ratio of peak areas of primary alcohols obtained with commercial 85 μm CAR-PDMS fiber, 65 μm DVB-PDMS and 1 μm present sputtered fiber.

Figure 10:
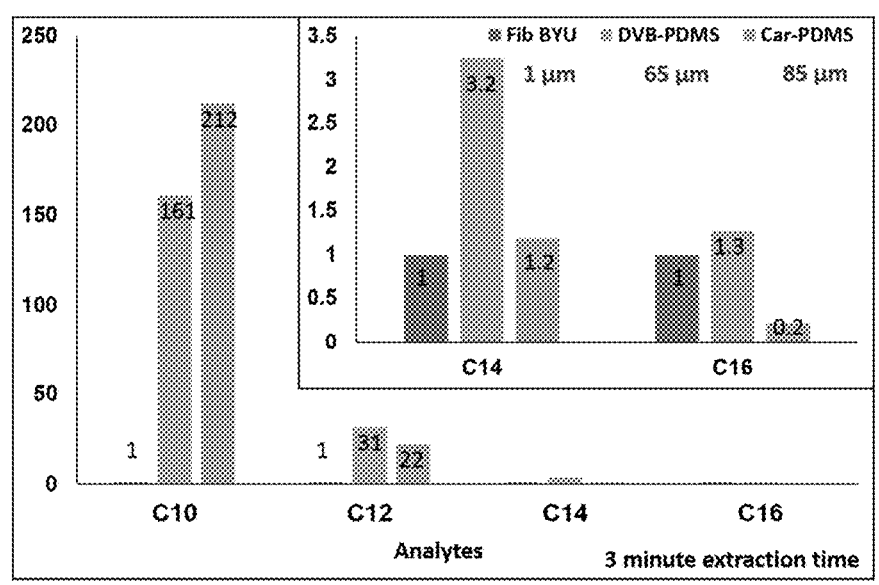

FIG. 10. Ratio of peak areas of saturated alkanes obtained with commercial 85 μm CAR-PDMS fiber, 65 μm DVB-PDMS and 1 μm present sputtered fiber.

Figure 11:
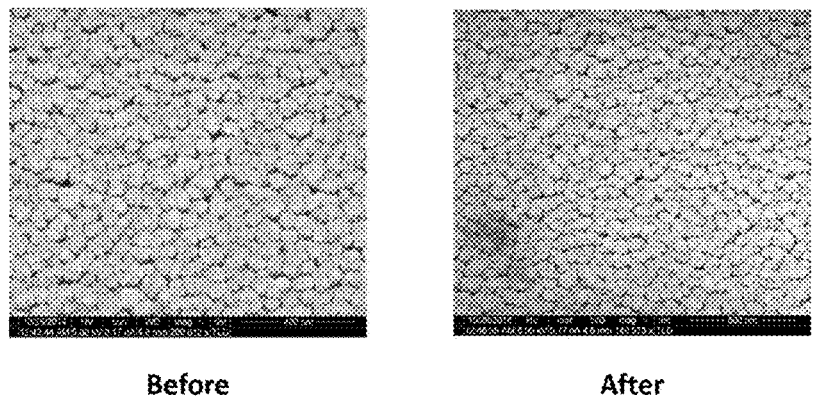

FIG. 11. SEM micrographs of sputtered silicon layer (1 hour sputtering) on silicon wafer before and after scotch-tape adhesion testing.

Figure 12:
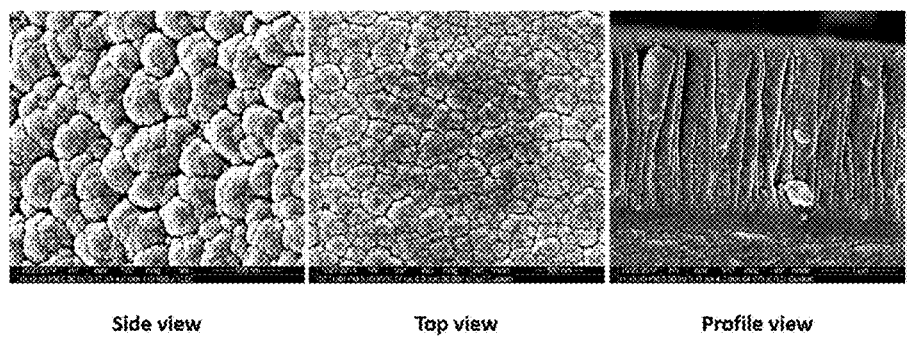

FIG. 12. SEM images of ~2.2 μm thick silicon coated present fibers.

DETAILED DESCRIPTION

Example

Experimental

The preparation of nanoporous silica coatings for SPME via sputtering consists of the following steps:

I. Silica Fiber Preparation

Polyimide-coated silica fibers (140 μm in diameter) were cut in lengths of 3.3 cm and the polyimide coating on the fibers was burned off. The resulting diameter of the fibers was 120-124 μm. The fibers were visually inspected for any left-over polyimide coating.

II. Sputter Deposition

Cut fibers were fixed onto the platen (sample holder) of a PVD 75 (sputter system from the Kurt J. Lesker Co.) in a way such that the fibers hang nearly vertically in the chamber. Silicon (99.999%) was DC magnetron sputtered at 4 mTorr and 200 W power. Argon was employed as the sputtering gas. Sputtering was done for different times to study the effect of thickness on the extraction capacities of the fibers.

III. Hydroxylation of the Silica Surface

Sputtered fibers were treated in piranha solution (7:3:: $H_2SO_4$:$H_2O_2$) at 85-90° C. for 45 minutes to introduce additional silanol groups on the sputtered silicon surface. This was followed by rinsing these fibers with ultra-high purity water and drying them in nitrogen for 15 minutes.

IV. Rendering the SPME Silicon Coating Hydrophobic

Silanization chemistry was used to introduce $C_{16}$ chains on the silica surface via chemical vapor deposition in a home-made oven. A liquid phase deposition of the silane should also be possible. The fibers were placed in the oven chamber, which was evacuated to a base pressure of 0.5 Torr. After that, 0.1 mL of n-octadecyldimethylmonomethoxysilane (C-18 silane) was directly injected into the preheated oven at 200° C. The vapors of the silane were allowed to remain in the chamber for 20 min. Finally, the chamber was purged three times to remove the unreacted $C_{18}$ silane.

V. Attachment of SPME Fibers

Finally, using epoxy glue (EPO-TEK 353ND-T), the fibers were attached to the plunger needle of SUPELCO SPME assemblies. The final length of the exposed fibers was 1.0 cm.

While sputtering silicon onto the fibers, witness silicon wafers were also sputtered so they could be characterized using XPS and water contact angle goniometry.

VI. GC-FID Conditions

The test mix consisted of 1 ppm each of decane ($C_{10}$), dodecane ($C_{12}$), tetradecane ($C_{14}$), and hexadecane ($C_{16}$) in water. The solution was made by dissolving 2 μL each of $C_{10}$, $C_{12}$, $C_{14}$, and $C_{16}$ in 10 mL of ethanol and then diluting 50 μL of this stock solution with 10 mL of ultra-high purity water to attain 1 ppm concentrations. For analysis, 5 mL of this solution was taken in a 20 mL SPME vial. The stock solution was stored at 4° C.

The GC column used was HP-5 5% phenyl methyl siloxane with capillary dimensions of 30.0 m×250 μm×0.25 μm. Fibers were preconditioned at 280° C. for 360 min. However, sometimes longer times were needed to precondition the fibers. GC conditions were: incubation time of the analyte solution in the vial: 5 min. at 40° C., headspace extraction time of the analytes: 10 minutes at 40° C., desorption conditions in the GC injection port: 280° C. for 1 minute. The initial column temperature was 70° C. with a ramp rate of 20° C./min up to 200° C. followed by a ramp rate of 30° C./min to 300° C., with a hold for 3 min at 300° C. The total run time for the analysis was 13.83 min. The fibers were baked for 10 min between the runs at 280° C.

Results

Figure 1:
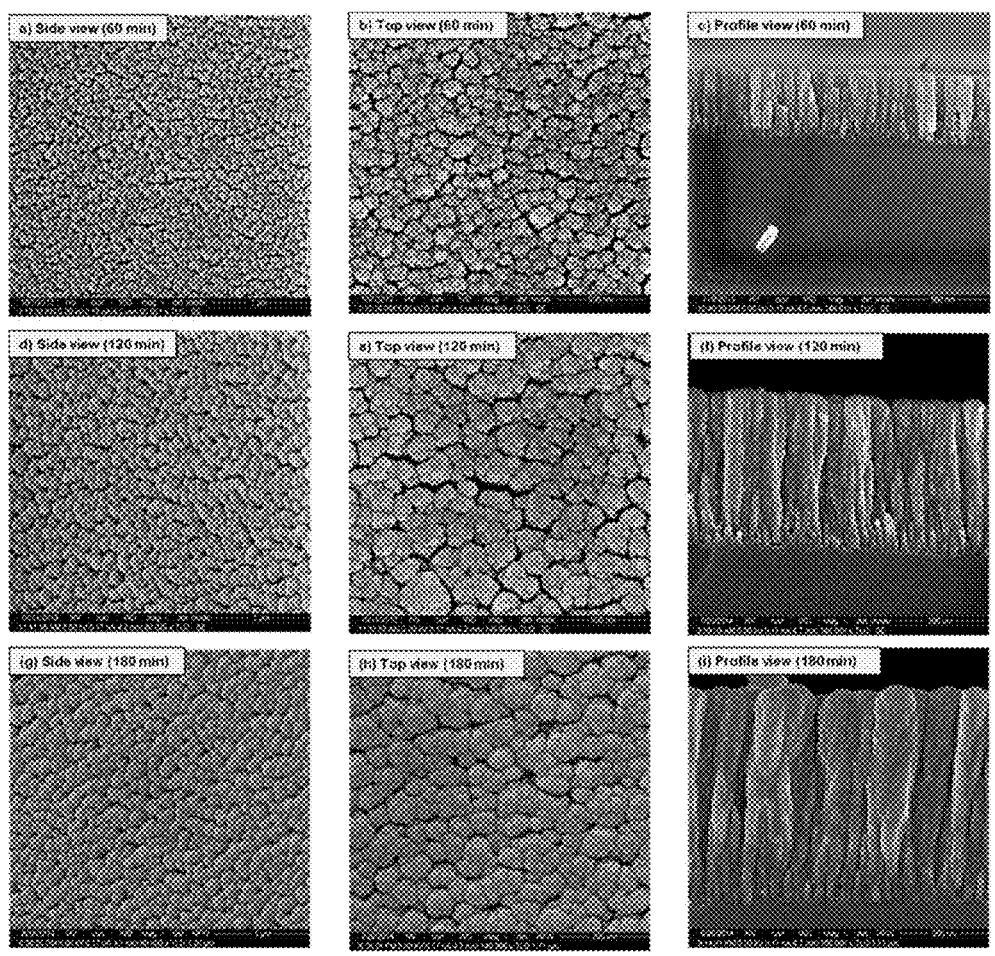
FIG. 1. SEM images of silica fibers sputtered with silicon at 4 mTorr. The fibers were positioned in the direction of the sputter target, but 1.5 cm off of the center of the target. Sputtering times were 60 min: (a) side view, (b) top view, (c) profile view, 120 min: (d) side view, (e) top view, and (f) profile view, and 180 min: (g) top view, (h) profile view. NOTE: in image (c), the profile view represents the bottom part of the fiber. The bottom point refers to the furthest part from the target and hence has lowest thickness, whereas (f) and (i) represent the top part, nearest to the target.

Silica coatings for SPME were prepared by sputtering silicon. This example was performed on silica fibers, but various other metal fibers could be used to enhance the mechanical stability of the fiber. The substrates were hanged vertically in the chamber, approximately perpendicular to the target. The fibers, after sputtering of silicon at 200 W DC magnetron power, were observed via SEM (FIG. 1). The resulting coatings were quite porous with vertical columnar structures.

This could be explained because of the lower mean free path of the sputtered silicon atoms due to a relatively high pressure in the chamber (4 mTorr) and relatively long throw distance (17-20 cm) (distance between the target and the fiber substrates). A lower mean free path means that the silicon atoms undergo multiple collisions before reaching the substrate and hence lack directionality. We calculate the mean free path of silicon atoms at 4 mTorr and other pressures using the following well-known equation:

$$\lambda = \frac{k_B T}{\sqrt{2}\, \pi d^2 p}$$

where, $\lambda$=mean free path, $k_B$=Boltzmann constant, T=temperature in K (298 K), d=diameter of the molecule (diameter of silicon atom is 222 pm), p=pressure in Pascal. Obviously, the application of this equation isn't quite correct here. We have assumed that all the atoms in the chamber are silicon, which is not the case. Nevertheless, this equation should provide a fairly accurate measure of the mean free paths of the present sputtered silicon atoms.

TABLE 1

Mean free paths of Si atoms at various pressures.

| Sputtering pressure (mTorr) | Mean free path of Si atom (cm) |
| --- | --- |
| 4 | 3.53 |
| 3 | 4.70 |
| 2 | 7.05 |
| 1 | 14.10 |

Table 1 shows the mean free path of Si atom at various sputtering pressures in the PVD 75 chamber. It is evident that the mean free path at 4 mTorr is rather small compared to the throw distance, hence leading to the vertical columnar structures observed on the present fibers instead of the type of structures that would be obtained in an oblique angle deposition.

Under the above deposition conditions, the vertical columnar structures showed some tapering as the thickness of the fiber decreased from top to bottom. For a 1 cm fiber sputtered for 3 h, the thickness was ca. 1.1 μm at the bottom of the fiber (closest to the target) and 0.86 μm at the top (furthest from the target). The tapered thicknesses from top to bottom were also seen with 2 h and 1 h sputtered fibers.

Overall, the vertical columnar structures seem to be beneficial as they are robust and showed good extraction capabilities.

After sputtering, the silicon fibers were treated with piranha solution. The rationale for treatment with this solution was to introduce additional silanol groups onto their surfaces, which in turn, would provide more binding sites for $C_{18}$ silane, and hence greater hydrophobicity. The C-18 silane was vapor deposited in a home made oven. Spectroscopic ellipsometry showed an increase in thickness of about 1.2 nm on a witness (non-sputtered) silicon wafer confirming the attachment of the $C_{18}$ silane.

Figure 2:
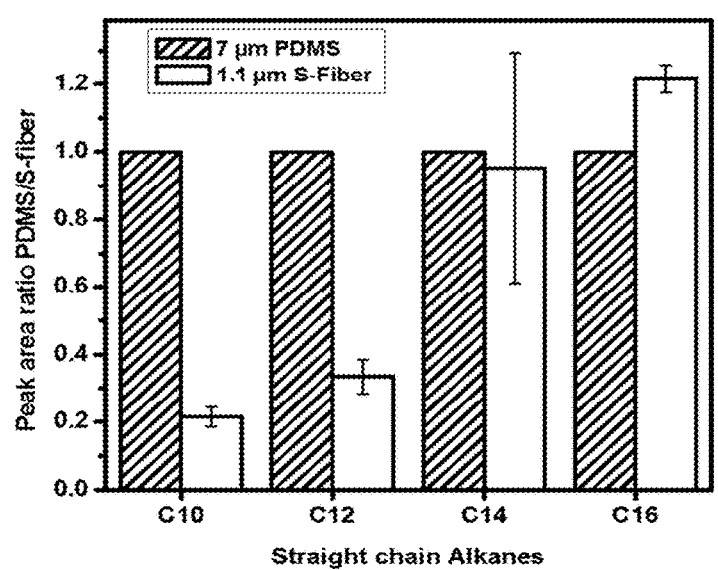
FIG. 2. Ratio of peak areas of straight chain alkanes obtained with commercial 7 μm PDMS fiber and ca. 1 μm present sputtered fiber. (Here, '7 μm' and 1 μm' refer to the thickness of the coatings on the fiber.)

As the thicknesses of the sputtered coatings increased, so did their extraction capacities. Therefore, comparatively thicker coatings were made by sputtering silicon for a longer period of time, e.g., three hours (as opposed to 1 or 2 hours) at 4 mTorr. Two of these fibers (fibers I & II) were tested using GC-FID (gas chromatography-flame ionization detector) analysis/detection and were compared to 7 μm PDMS commercial fibers. The increase in thickness of the sputtered silicon fibers enhanced extraction capacities, i.e., more signal was obtained from the thicker coatings. For higher molecular weight compounds, $C_{14}$ and $C_{16}$, the extraction efficiencies were better with the present fiber as compared to commercial PDMS 7 μm fibers (FIG. 2).

Figure 3:
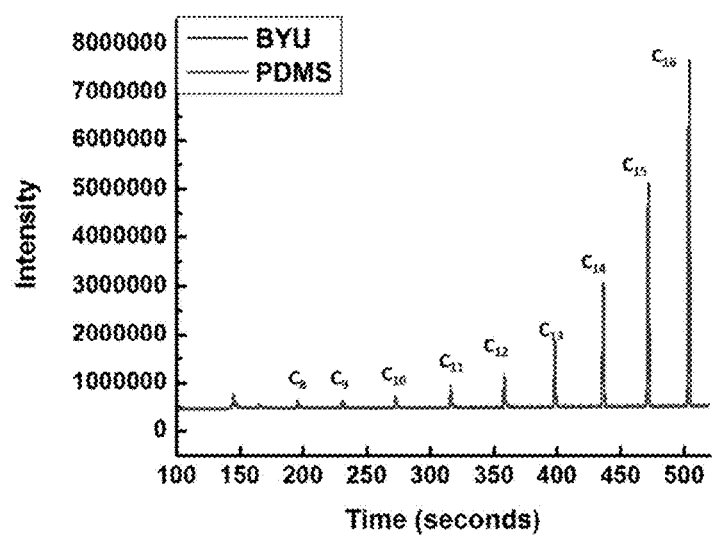
FIG. 3. Gas chromatograms of saturated alkanes ($C_8$-$C_{16}$) obtained with commercial 7 μm PDMS fiber and present ca. 1 μm sputtered fiber FIG. 4. Ratio of peak areas of primary alcohols obtained with commercial 7 μm PDMS fiber and present sputtered fiber ca. 1 μm (S-fiber)

A mixture of alkanes ($C_8$-$C_{16}$) was separated at the University of Tasmania with the same trends. The sputtered fibers (~1 μm) outperformed the PDMS (7 μm) fibers, especially in the high mass regime ($C_{13}$-$C_{16}$) (FIG. 3).

Figure 4:
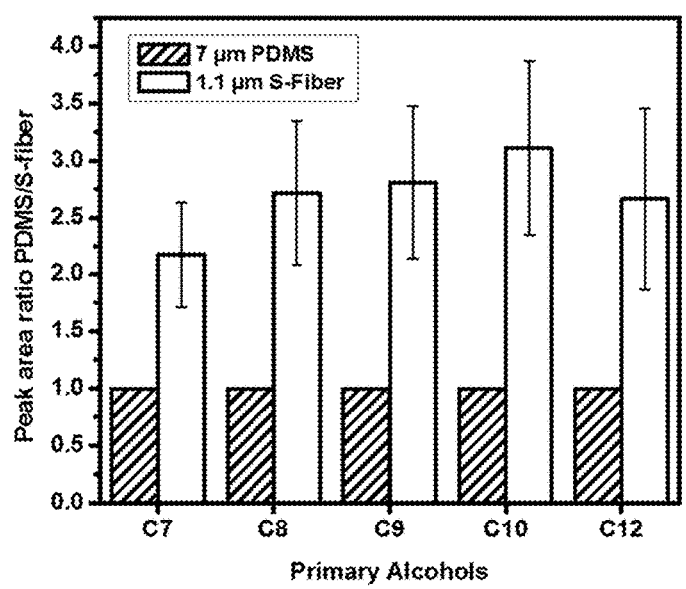

The sputtered fibers were also used for separating a mix of primary alcohols, where they showed greater selectivity for the higher molecular weight analytes than the commercial PDMS 7 μm fiber (see FIG. 4). The extraction conditions were the same as used for extracting the alkanes. The results suggested that the present fibers had unique selectivity for polar alcohols as compared to PDMS fibers.

In addition, these fibers were also used for some real world samples, including sea water extract and beer analysis. 'James Boag's Premium Light' Launceston, Australian beer was analyzed. The extraction conditions were: sample volume: 5 mL beer directly from the bottle; extraction temperature: 45° C.; extraction time: 10 minutes; desorption temperature: 280° C.; desorption time: 1 minute; initial column temperature: 60° C., ramp 10° C./min till 240° C., ramp 20° C./min till 280° C. and hold for 3 minutes.

No attempts were made to identify the peaks; rather qualitative comparisons were made between the chromatograms obtained from the present sputtered fiber and the 7 μm PDMS counterpart. FIG. 6 shows that the present fiber outperformed the commercial PDMS 7 μm fiber, especially in the high mass range region.

We also analyzed a sea water extract. Tens of gallons of sea water were passed through a $C_{18}$ solid phase extraction (SPE) cartridge and the eluent was dried. The dried extract was dissolved in 80:20 water:methanol mixture. 25 μL of this solution was added to 5 mL of ultra-pure water and used for analysis. The extraction conditions were: sample volume: 5 mL; extraction temperature: 40° C.; extraction time: 8 hours; desorption temperature: 280° C.; desorption time: 1 minute; initial column temperature: 60° C., ramp 3° C./min till 240° C., ramp 20° C./min till 280° C. and hold for 3 minutes.

FIG. 7 compares the results of analysis of sea water extract using sputtered fiber (~1 μm) and PDMS fiber (7 μm) which depicts some interesting findings. BYU fiber was able to extract some peaks that the commercial PDMS fiber was not able to extract (see oval). It is important to mention that these peaks were in the low mass regime, indicating unique selectivities of the present fiber, presumably due to unreacted —OH groups and C18 chains decorating the surface. Blue (dotted) ovals show higher extraction and unique peaks extracted by the present fiber in the mid-mass range regime. The rise in baseline around 450 second in case of the sputtered fiber indicates that higher quantities of analytes were extracted as compared to PDMS fiber. 2-D GC (GC× GC) would be tried in the future to isolate all the separate compounds.

To understand why the present fibers perform better in the high mass regime, it is important to understand the mechanism of action of the present fibers. While not limited to a theory, PDMS is an example of liquid stationary phase, which extracts analytes via absorption. The amount of analyte extracted depends on the concentration of analyte in the sample matrix and follows a linear trend. On the other hand, solid coatings (for example the present sputtered fibers) appears to work on the principle of adsorption, that is analytes stick on specific sites on the coatings and as there are finite number of sites, the extraction process becomes competitive at higher concentrations.

While not limited to a theory, assume that the solid coating has a finite number of 'sites' on the surface. A low molecular weight analyte–'analyte$_1$' and high molecular weight analyte–'analyte$_2$' are being extracted:

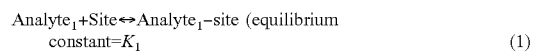

$$\text{Analyte}_1 + \text{Site} \leftrightarrow \text{Analyte}_1\text{-site (equilibrium constant} = K_1) \quad (1)$$

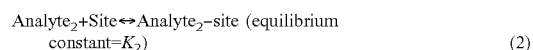

$$\text{Analyte}_2 + \text{Site} \leftrightarrow \text{Analyte}_2\text{-site (equilibrium constant} = K_2) \quad (2)$$

(analyte$_1$-site and analyte$_2$-site refer to complexes between the respective analyte and site)

As analyte$_2$ is higher molecular weight, its extraction would be enthalpy favored and, therefore, under the extraction conditions used $K_2 > K_1$ Reversing (1) and adding to (2):

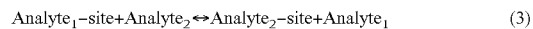

$$\text{Analyte}_1\text{-site} + \text{Analyte}_2 \leftrightarrow \text{Analyte}_2\text{-site} + \text{Analyte}_1 \quad (3)$$

The above equation describes how a higher molecular weight specie would displace lower molecular weight analytes. The equilibrium constant of the displacement reaction in (3) is given by $K_2/K_1$.

To demonstrate that the present sputtered fibers follow an adsorption mechanism, we created an extraction profile separating a mixture of octanol, nonanol, decanol and dodecanol (1 ppm each in water). The mixture was extracted at 40° C. for 1, 3, 5, 7, 10, and 15 minutes. The peak areas for different analytes were recorded as a function of extraction time (see FIG. 8). Extraction conditions were: sample volume: 5 mL; extraction temperature: 40° C.; extraction time: variable; desorption temperature: 280° C.; desorption time: 1 minute; initial column temperature: 70° C., ramp 10° C./min till 200° C., ramp 30° C./min till 300° C. and hold for 3 minutes.

It is evident from FIG. 8 that the initial response for dodecanol was quite small at the 1 minute extraction time. As the duration of extraction increased, the response of dodecanol increased significantly at the expense of loss of response of other lower molecular weight analytes. Therefore, the sputtered fibers can be used for two types of extraction:

(1) Short time extraction: extract lower molecular weight species (2) Longer time extraction: extract higher molecular weight species It is worth emphasizing that even though PDMS has a different mechanism of extraction than the present sputtered fibers, it is one of the most commonly used commercial extraction phase. Hence, a comparison of PDMS with the present fibers is reasonable. Nevertheless, we have extended this comparison to other solid extraction phases—
(i) Carboxen-PDMS (CAR-PDMS) 85 µm fiber
  a. Used for low molecular weight analytes
(ii) PDMS-DVB 65 µm fiber
  a. Used for high molecular weight analytes We compared the response of the present sputtered fiber with the above mentioned solid adsorption coatings using a mixture of alcohols and alkanes.

The mixture of alcohols consisted of $C_7$, $C_8$, $C_9$, $C_{10}$ and $C_{12}$ primary alcohols (1 ppm in water). The separation conditions were similar as employed earlier for separation of alcohols, except that the desorption temperature was kept at 260° C. for all the fibers and the extraction time was 3 minutes. The desorption temperature value was influenced by the upper operating temperature limit for comparison adsorbent fibers. FIG. 9 compares the response of ~1 µm thick sputtered fiber with 85 µm CAR-PDMS and 65 µmDVB-PDMS fibers.

For $C_7$ alcohol the PDMS-DVB gave 58 times and CAR-PDMS gave 45 times the response of sputtered fiber. Considering that extraction profiles scale down linearly with thickness, we are actually performing better than the other two fibers. The ratios become more favorable as we go to higher molecular weight analytes. Even for $C_8$ alcohol, CAR-PDMS only does 3 times better than sputtered fibers, despite being 85 times thicker. For $C_{10}$, we outperform the 85 times thicker CAR-PDMS and give ⅓ response as the 65 times thicker DVB-PDMS. The most interesting finding was that CAR-PDMS was not able to extract $C_{12}$ alcohol at all. Overall, for higher molecular weight compounds, we had comparable and in some cases better response than the coatings that were 85 times thicker than ours.

After outperforming thicker adsorbent coatings in separating alcohols, we tested the alkanes. We have a unique selectivity for alcohols, other fiber might not. The comparison fibers in question are used extensively for extraction of hydrophobic compounds, like alkanes. Therefore, a comparison for separating alkanes would be valuable. The separation conditions were same as mentioned above in case of alcohols.

FIG. 10 shows the comparison of the present fiber with two other commercial adsorbent coatings for the extraction of a mixture of $C_{10}$, $C_{12}$, $C_{14}$, and $C_{16}$ alkanes. The results follow the same trend. For $C_{10}$, CAR-PDMS gave 212 times and PDMS-DVB gave 161 times the response of the present fiber, which was expected as the present fibers have shown to work better for higher molecular weight analytes. The ratios decrease for $C_{12}$ and for $C_{14}$, CAR-PDMS gave 1.2 times and DVB-PDMS gave 3.2 times the response of the present fiber. Further, for $C_{16}$, the present 1 µm thick fiber outperformed the 85 µm thick CAR-PDMS fiber with ease, giving 5 times the response. 65 µm thick DVB-PDMS gave 1.3 times the response of the present fiber.

Also, the present sputtered fibers were free of any carry-over effects, whereas, the other two solid adsorbent coatings had significant carryover effects.

To show the robustness of the present sputtered films, we performed a scotch-tape adhesive test. This is one of the yard-sticks to measure the adhesion of the films to the substrates. We sputtered Si using the same instrument, conditions and geometry onto planar silicon wafers for 1 hour and did SEM on it (see FIG. 11 (Before)). A piece of scotch tape was pasted on the surface and then removed. The residue leftover from the tape was cleaned by sonicating the wafer in a vial full of acetone. The SEM after the test showed no damage to the structures (see FIG. 11 (After)).

As the thickness of the sputtered coatings increases, so did the response. On the same lines, in order to enhance the extraction capabilities, we have sputtered a ~2.2 µm silicon coating on silica fibers. FIG. 12 shows the SEM of the present thicker coatings. As expected, these thicker coatings showed higher extraction capacities (larger signals) compared to their thinner counterparts.

CONCLUSION

The SPME coating prepared by sputtering can provide robust coatings with high porosities. The method could be applied to produce various metal or metal oxides coatings. Moreover, the selectivity of the coating could be manipulated using different chemistries on the surface (example silanization chemistry on silica coatings to yield desired selectivities). Sputtering provides a better control over coating thickness, with high reproducibility. The present sputtered fibers were able to outperform thicker liquid and solid coatings, especially in the high mass regime, providing huge potential for a faster analysis.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for extracting analytes from a gas or liquid phase comprising exposing the phase to an extractive adsorptive phase wherein:
   the extractive adsorptive phase comprises a porous coating on a substrate;
   the porous coating includes:
      columnar nanostructures which are close to perpendicular to a surface plane of the substrate and mutually supporting; and
      nanospaces at boundaries between adjacent columnar nanostructures; and
   the porous coating is tapered with length of columnar nanostructures decreasing in length along a line over the substrate.

2. The method of claim 1, wherein the substrate is a needle.

3. The method of claim 2, wherein a thickness of the porous coating is circumferentially constant.

4. The method of claim 1, wherein the porous coating comprises a silanized silica, a silanized silicon, or both.

5. The method of claim 1, wherein the porous coating comprises aluminum, carbon, silicon, titanium, or combinations thereof.

6. The method of claim 1, wherein the porous coating comprises zirconium.

7. The method of claim 1, wherein the porous coating comprises alumina, silica, silicone, titania, or combinations thereof.

8. The method of claim 1, wherein the porous coating comprises zirconia.

9. The method of claim 1, wherein the substrate comprises a flexible fiber.

10. A method for extracting analytes from a gas or liquid phase comprising exposing the phase to an extractive adsorptive phase, wherein:

the extractive adsorptive phase comprises a porous coating on a substrate;
the porous coating includes:
  columnar nanostructures which are close to perpendicular to a surface plane of the substrate and mutually supporting; and
  nanospaces at boundaries between adjacent columnar nanostructures; and
the substrate is a SPME needle; and
a thickness of the coating is circumferentially constant and tapered along a length of the SPME needle, with longer columnar nanostructures at the point of the needle, and becoming thinner with shorter columnar nanostructures as the distance from the point increases.

11. The method of claim 10, wherein the porous coating comprises a silanized silica, a silanized silicon, or both.

12. An apparatus in which analytes are adsorbed onto an extractive phase and subsequently desorbed, the apparatus comprising:
  an extractive adsorptive phase comprising a porous coating upon a substrate, wherein the porous coating:
    includes columnar nanostructures which are close to perpendicular to a surface plane of the substrate and mutually supporting;
    includes nanospaces at boundaries between adjacent columnar nanostructures; and
    is tapered with length of columnar nanostructures decreasing in length along a line over the substrate;
  a structure for introducing a liquid or gas containing analytes to a surface of the substrate for sufficient time to allow the analytes to adsorb upon the extractive phase;
  a structure for desorbing analytes from the surface into a gas stream; and
  a detector for detecting analytes in the gas stream.

13. The method of claim 12, wherein the porous coating comprises aluminum, carbon, silicon, titanium, zirconium, or combinations thereof.

14. The method of claim 12, wherein the porous coating comprises alumina, silica, silicone, titania, zirconia, or combinations thereof.

15. The method of claim 12, wherein the substrate comprises a flexible fiber.

16. The method of claim 10, wherein the porous coating comprises aluminum, carbon, silicon, titanium, zirconium, or combinations thereof.

17. The method of claim 10, wherein the porous coating comprises alumina, silica, silicone, titania, zirconia, or combinations thereof.

18. The method of claim 10, wherein the SPME needle comprises a flexible fiber.

19. The method of claim 12, wherein the porous coating comprises a silanized silica, a silanized silicon, or both.

20. The apparatus of claim 12 wherein the substrate is a SPME needle, and the thickness of the coating is circumferentially constant and tapered along the length of the needle, with longer columnar nanostructures at the point of the needle, and becoming thinner with shorter columnar nanostructures as the distance from the point increases.

* * * * *